(12) United States Patent
Kay et al.

(10) Patent No.: US 10,362,780 B2
(45) Date of Patent: Jul. 30, 2019

(54) OXYGEN SUPPLY FOR ORGAN PERFUSION SYSTEMS

(71) Applicant: Organox Limited, Oxford (GB)

(72) Inventors: Stuart Brian William Kay, Cambridge (GB); Sebastien Antoine Yves Cuvelier, Cambridge (GB); Jonathan Richard Oakley, Cambridge (GB); Leslie James Russell, Oxford (GB); Peter John Friend, Oxford (GB); Constantin C. Coussios, Oxford (GB)

(73) Assignee: Organox Limited, Oxford (GB)

(*) Notice: Subject to any disclaimer, the term of this patent is extended or adjusted under 35 U.S.C. 154(b) by 141 days.

(21) Appl. No.: 14/357,078

(22) PCT Filed: Nov. 8, 2012

(86) PCT No.: PCT/GB2012/052783
§ 371 (c)(1),
(2) Date: May 8, 2014

(87) PCT Pub. No.: WO2013/068753
PCT Pub. Date: May 16, 2013

(65) Prior Publication Data
US 2015/0004677 A1 Jan. 1, 2015

(30) Foreign Application Priority Data
Nov. 10, 2011 (GB) .................. 1119420.6

(51) Int. Cl.
*A01N 1/02* (2006.01)
*A61M 1/16* (2006.01)

(52) U.S. Cl.
CPC .............. *A01N 1/0247* (2013.01); *A01N 1/02* (2013.01); *A61M 1/1698* (2013.01)

(58) Field of Classification Search
CPC ...... A01N 1/0247; A01N 1/02; A61M 1/1698
See application file for complete search history.

(56) References Cited

U.S. PATENT DOCUMENTS

| 3,772,153 A | 11/1973 | De Roissart |
| 4,493,692 A * | 1/1985 | Reed ............... A61M 1/32 128/DIG. 3 |
| 5,157,930 A | 10/1992 | McGhee et al. |

(Continued)

FOREIGN PATENT DOCUMENTS

| DE | 197 02 098 A1 | 7/1998 |
| DE | 197 15 152 A1 | 10/1998 |

(Continued)

OTHER PUBLICATIONS

International Search Report and Written Opinion dated Jul. 5, 2013 for PCT/GB2012/052781 filed Nov. 8, 2012.

(Continued)

*Primary Examiner* — Jonathan M Hurst
(74) *Attorney, Agent, or Firm* — Wegman Hessler

(57) ABSTRACT

A perfusion system for the perfusion of an organ comprises a perfusion fluid circuit (16) for circulating perfusion fluid through the organ, oxygenation means (14) for adding oxygen into the perfusion fluid, and an oxygen supply arranged to supply oxygen to the oxygenation means. The oxygen supply comprises an oxygen concentrator.

6 Claims, 2 Drawing Sheets

(56) References Cited

U.S. PATENT DOCUMENTS

| | | | |
|---|---|---|---|
| 5,462,416 A | 10/1995 | Dennehey et al. | |
| 5,695,717 A * | 12/1997 | Polaschegg | A61M 1/1698 210/500.3 |
| 6,582,953 B2 | 6/2003 | Brasile | |
| 6,642,045 B1 | 11/2003 | Brasile | |
| 6,673,594 B1 * | 1/2004 | Owen | A01N 1/02 435/284.1 |
| 7,491,261 B2 * | 2/2009 | Warren | B01D 53/0407 95/130 |
| 2004/0170950 A1 * | 9/2004 | Prien | A01N 1/0247 435/1.2 |
| 2004/0235142 A1 | 11/2004 | Schein et al. | |
| 2004/0238444 A1 | 12/2004 | Ragusa | |
| 2005/0221269 A1 | 10/2005 | Taylor et al. | |
| 2005/0255442 A1 | 11/2005 | Brassil et al. | |
| 2006/0148062 A1 | 7/2006 | Hassanein et al. | |
| 2006/0224334 A1 | 10/2006 | Zhang et al. | |
| 2007/0227360 A1 * | 10/2007 | Atlas | A61M 16/10 96/121 |
| 2007/0275364 A1 | 11/2007 | Hassanein et al. | |
| 2008/0017194 A1 | 1/2008 | Hassanein et al. | |
| 2008/0032398 A1 | 2/2008 | Cannon et al. | |
| 2009/0197241 A1 | 8/2009 | Fishman et al. | |
| 2009/0197324 A1 * | 8/2009 | Fishman | A01N 1/02 435/284.1 |
| 2010/0028979 A1 | 2/2010 | Faulkner et al. | |
| 2010/0143192 A1 | 6/2010 | Myrick et al. | |
| 2010/0330547 A1 | 12/2010 | Tempelman et al. | |
| 2011/0076666 A1 | 3/2011 | Brassil | |
| 2011/0136096 A1 | 6/2011 | Hassanein et al. | |
| 2012/0178150 A1 | 7/2012 | Tempelman et al. | |

FOREIGN PATENT DOCUMENTS

| | | |
|---|---|---|
| DE | 100 15 807 A1 | 10/2001 |
| EP | 0 109 373 A2 A2 | 5/1984 |
| EP | 1 168 913 B1 | 11/2005 |
| WO | WO 96/29865 A1 | 10/1996 |
| WO | WO 02/077579 A1 | 10/2002 |
| WO | WO 2004/089085 A2 | 10/2004 |
| WO | WO 2006/042138 A2 | 4/2006 |
| WO | WO 2006/118990 A2 | 11/2006 |
| WO | WO 2007/124044 A2 | 11/2007 |
| WO | WO 2008/150587 A2 | 12/2008 |
| WO | WO 2009/020412 A1 | 2/2009 |
| WO | WO 2012/170633 A1 | 12/2012 |

OTHER PUBLICATIONS

International Search Report and Written Opinion dated Mar. 6, 2013 for PCT/GB2012/052783 filed Nov. 8, 2012.
International Preliminary Report on Patentability dated May 13, 2014 for PCT/GB2012/052783 filed Nov. 8, 2012.
Search Report Under Section 17 dated Mar. 8, 2012 for GB 1119420.6 filed Nov. 10, 2011.
International Search Report and Written Opinion dated Jun. 14, 2013 for PCT/GB2012/052782 filed Nov. 8, 2012.
International Preliminary Report on Patentability dated May 22, 2014 for PCT/GB2012/052782 filed Nov. 8, 2012.
Search Report Under Section 17 dated Mar. 7, 2012 for GB 1119418.0 filed Nov. 10, 2011.
Search Report Under Section 17 dated Mar. 7, 2012 for GB 1119419.8 filed Nov. 10, 2011.
International Preliminary Report on Patentability dated May 22, 2014 for PCT/GB2012/052781 filed Nov. 8, 2012.
Search Report Under Section 17 dated Mar. 8, 2012 for GB 1119417.2 filed Nov. 10, 2011.
Examination Report Under Section 18(3) dated Feb. 3, 2017 for GB 1408217.6 filed Nov. 8, 2012.
Non-final Office Action dated Mar. 11, 2019 for U.S. Appl. No. 15/338,841.

* cited by examiner

OXYGEN SUPPLY FOR ORGAN PERFUSION SYSTEMS

CROSS-REFERENCE TO RELATED APPLICATIONS

This application claims the priority filing benefit of International PCT Application PCT/GB2012/052783 filed Nov. 8, 2012 and published under PCT 21(2) in the English language and Great Britain Patent Application Serial No. 1119420.6 filed Nov. 10, 2011. All of the above listed applications are herein incorporated by reference.

FIELD OF THE INVENTION

The present invention relates to perfusion systems for bodily organs, for example human organs, such as the liver, pancreas, kidney, small bowel, but also other organs including non-human organs. In particular the invention relates to the supply of oxygen for such systems and the control of the content of perfusion fluids in such systems.

BACKGROUND TO THE INVENTION

It is known, for example from EP 1 168 913, to provide a system for extracorporeal organ perfusion in which a human or non-human organ can be preserved, for example prior to transplant into a patient. The system typically comprises a reservoir for perfusion fluid (or perfusate), which may be blood or another perfusion solution, and a circuit for circulating the fluid through the organ. The circuit typically also comprises an oxygenator or other device for adding oxygen, carbon dioxide, or other substances into the blood, from a source which typically comprises a pressurized gas cylinder.

SUMMARY OF THE INVENTION

The present invention provides a perfusion system for the perfusion of an organ, the system comprising a fluid circuit for connection to the organ and arranged to supply perfusion fluid (perfusate) to the organ, and oxygenation means arranged to add oxygen into the fluid as the fluid circulates in the circuit, and an oxygen supply arranged to supply oxygen to the oxygenation means.

The oxygen supply may comprise an oxygen concentrator. The oxygen concentrator may have an inlet arranged to receive air, which may be at atmospheric pressure. The oxygen concentrator may comprise nitrogen extraction means for extracting nitrogen from the air. The oxygen concentrator may comprise an outlet from which gas can be fed to the oxygenator.

The system may further comprise an air supply arranged to supply air to the oxygenation means whereby the oxygenation means can add carbon dioxide to the perfusion fluid.

The oxygen concentrator may comprise a compressor arranged to pump the gas through the nitrogen extraction means. The pump may be arranged to pump gas to the oxygenation means. Some of that gas may be arranged to bypass the nitrogen extraction means, for example passing through a separate supply duct, to provide the gas necessary to control CO2 in the perfusate.

The system may further comprise an oxygen control valve arranged to control the flow rate of oxygen from the oxygen concentrator to the oxygenation means.

The system may further comprise oxygen measuring means arranged to measure the oxygen content in the perfusion fluid. The system may further comprise control means arranged to monitor the measured oxygen content. The control means may be arranged to control the oxygen control valve in response to the measured oxygen content. For example it may be arranged to maintain the oxygen content within a target range. The range may be defined by upper and lower limits, or just a lower limit.

The system may include an air control valve arranged to control the flow rate of air from the air supply to the oxygenation means.

The system may further comprise carbon dioxide measuring means arranged to measure the carbon dioxide content in the perfusion fluid. The system may include control means arranged to monitor the measured carbon dioxide content and to control the air control valve in response to the measured carbon dioxide content. For example the control means may be arranged to maintain the carbon dioxide content within a target range. In this case the oxygenation means is arranged both to add oxygen into the fluid and extract carbon dioxide from the fluid, and therefore serves as a gas content adjustment means for adjusting both oxygen and carbon dioxide level. However it will be appreciated that separate adjustment means can be provided, one for oxygen and one for carbon dioxide.

The system may further comprise an analysis duct through which the fluid can flow to bypass the organ. The measuring means may be arranged to measure the fluid in the analysis duct.

The measuring means may be arranged to operate during perfusion of the organ. The control means may be arranged to operate during perfusion of the organ to maintain the target range or ranges during perfusion.

In each case where a target range is referred to above, the range may be defined by upper and lower limits, or just a lower limit, or just an upper limit.

The system may further comprise a user interface arranged to enable a user to input at least one limit of said range, or at least one of said ranges. For example the user interface may be arranged to enable a user to input one or both limits of the target oxygen content, or one or both limits of the target carbon dioxide content.

Preferred embodiments of the present invention will now be described by way of example only with reference to the accompanying drawings.

BRIEF DESCRIPTION OF THE DRAWINGS

Referring to FIG. 1, a perfusion system according to an embodiment of the invention generally comprises a sling 10 in which an organ can be supported, a fluid reservoir 12, an oxygenator 14, and a perfusion circuit 16 arranged to circulate fluid between the reservoir, the organ, and the oxygenator during perfusion. A controller 18 is arranged to control the functioning of the system as will be described in more detail below.

Figure 1:
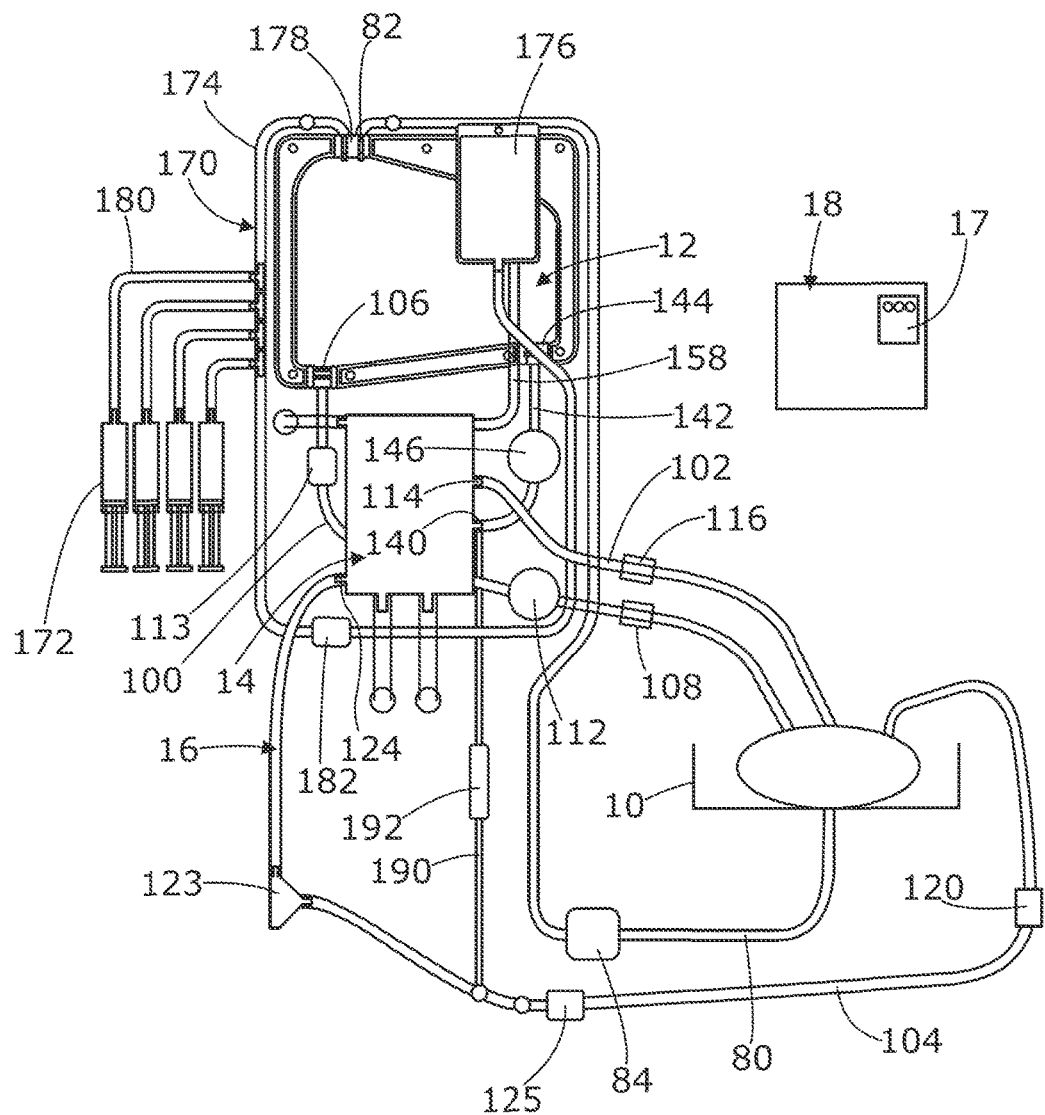
FIG. 1 is a schematic diagram of a perfusion system according to an embodiment of the invention.

An acities duct 80 is connected at one end to a drainage hole in the bottom of the sling 10 and at the other end to an acities return port 82 in the top of the fluid reservoir 12. An acities pump 84 is provided in the acities duct 80 to pump acities from the sling 10 back up into the reservoir 12.

The perfusion circuit 16 further comprises a portal duct 100, a hepatic artery duct 102 and an inferior vena cava (IVC) duct 104. The portal duct 100 has one end connected to an outlet port 106 in the fluid reservoir and the other end attached to a portal vein connector 108. A flow control valve, in the form of a pinch valve 112 having a variable degree of opening, is provided in the portal duct 100 and is connected to the controller 18. The controller 18 is arranged to vary the degree of opening of the pinch valve 112 so as to control the rate of flow of fluid from the reservoir 12 to the portal vein of a liver. The hepatic artery duct 102 has one end connected to a first outlet port 114 of the oxygenator 14 and the other end attached to a hepatic artery connector 116. A flow sensor 113 is arranged to measure the rate of fluid flow in the portal vein duct 100 and is arranged to output a signal indicative of the flow rate of fluid in the portal vein 100. The output of the flow sensor 113 is connected to the controller 18 which can therefore monitor the flow rate in the portal vein duct 100. The IVC duct 104 has one end attached to a vena cava connector 120 and its other end connected to an inlet port 124 of the oxygenator 14. A pump 123 is provided in the IVC duct 104 having its inlet connected to the vena cava connector 120 and its outlet connected to the inlet port 124 of the oxygenator 14. The pump 123 is arranged to pump fluid from the IVC duct 104 into the oxygenator 124. The pump 123 is a variable speed pump and is connected to, and controlled by, the controller 18. An IVC flow sensor 125 is arranged to measure the rate of fluid flow in the IVC duct 104 and is arranged to output a signal indicative of the flow rate of fluid in the IVC duct 104. The output of the flow sensor 125 is connected to the controller 18 which can therefore monitor the flow rate in the vena cava duct. The controller 18 is also arranged to measure the flow rate in the arterial duct 102 by determining the difference between the flow measured by the flow sensor 125 in the IVC duct 104 and that measured by flow sensor 113 in the portal vein duct 100.

The oxygenator 14 has a second outlet port 140 which is connected by a pressure control duct 142 to a further port 144 in the fluid reservoir 12. A flow control valve, in the form of a pinch valve 146, having a variable degree of opening, is provided in the pressure control duct 142 and is connected to the controller 18 so that the controller can vary the degree of opening of the pinch valve 146 thereby to control the return flow of fluid from the oxygenator 14 to the reservoir 12. This, together with the pump 123, is used to control the pressure of fluid flowing to the organ through the hepatic artery duct 102, as well as the pressure of the fluid in the IVC duct 104 flowing away form the organ.

Figure 2:
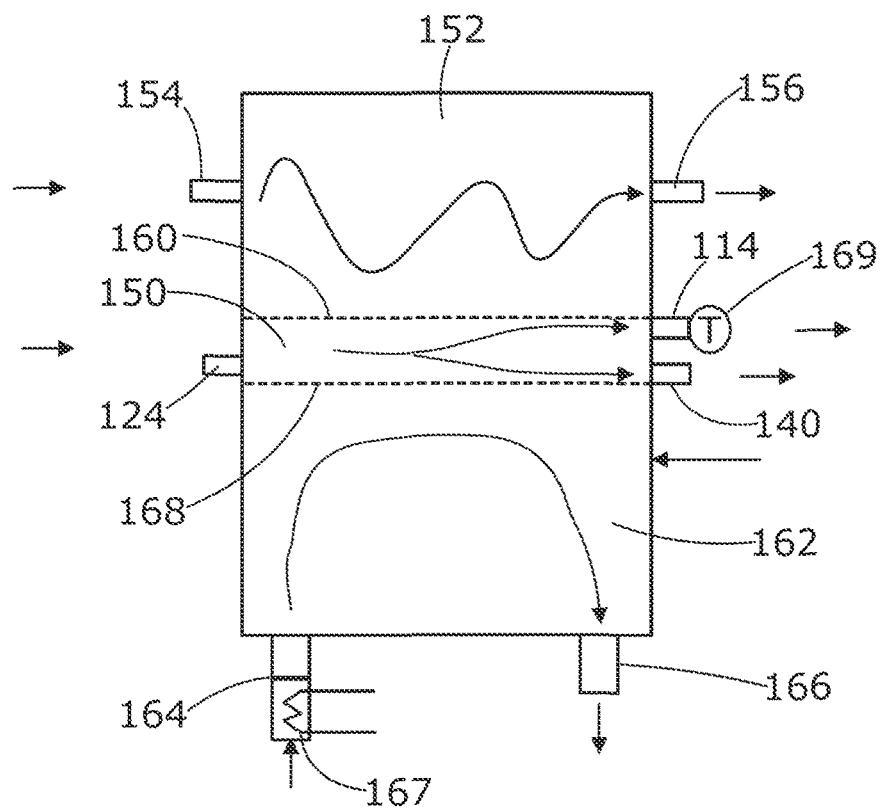
FIG. 2 is a schematic diagram of an oxygenator forming part of the system of FIG. 1.

Referring to FIG. 2, the oxygenator, which is shown schematically, comprises a through duct 150 arranged to carry fluid from the inlet port 124 to the two outlet ports 114, 140. An oxygen chamber 152 has an inlet port 154 for connection to an oxygen supply and an air supply, and an outlet or vent port 156 for venting the oxygen and air from the oxygen chamber. A vent 158 is connected at its lower end to the through duct 150 and extends upward so that its upper end is approximately level with the top of the reservoir 12. This vent 158 is closable, and is arranged to be opened during filling of the fluid circuit to vent air from the oxygenator, but is closed during perfusion. A permeable membrane 160 between the oxygen chamber 152 and the through duct 150 allows oxygen in the oxygen chamber 152 to oxygenate fluid, which may be blood, in the through duct 150. The membrane 160 also allows $CO_2$ in the perfusate to pass out of the perfusate through the membrane into the air. A water chamber or duct 162 is also connected to a water inlet port 164 and a water outlet port 166, and is separated from the through duct 150 by a thermally conductive wall 168. This allows water, or another suitable thermal control fluid, to be circulated through the oxygenator 14 to control the temperature of the perfusion fluid. A heater 167 is provided to heat water entering the oxygenator via the water inlet port 164, and a thermometer 169 is provided to measure the temperature of the perfusate flowing out of the oxygenator into the hepatic artery duct 102. The heater 167 and the thermometer 169 are connected to the controller 18 which is arranged to measure and monitor the temperature of the perfusate supplied to the organ and control the heater 167 so as to maintain the perfusate temperature at a desired level, for example within a target temperature range.

It will be appreciated that other devices can be used for adding oxygen and carbon dioxide into the perfusate. For example a bubbler can be used, instead of the type of oxygenator shown in FIG. 3, which bubbles the concentrated oxygen through the perfusate. Also, instead of one device which brings a gas into contact with the perfusate and in which the oxygen and carbon dioxide content of the gas are controlled, the system can include separate devices one for each gas.

Referring back to FIG. 1, a nutrient control circuit 170 comprises a set of syringes 172, in this case four, each containing a respective nutrient, and a nutrient feed duct 174 which has one end connected to a separate fluid reservoir 176 and the other end connected to a nutrient inlet port 178 in the top of the main fluid reservoir 12. Each of the syringes 172 is connected to the nutrient feed duct 174 by a respective nutrient input duct 180. A nutrient pump 182 is arranged in the nutrient feed duct 174 to pump fluid through the nutrient feed duct from the nutrient feed reservoir 176 into the main reservoir 12 via the nutrient inlet port 178. The pump 182 and the syringes 172 are controlled by the controller 18 so that the rate at which each of the nutrients is fed into the reservoir 12 is controlled.

A small diameter fluid analysis duct 190 has one end connected to the IVC duct 104, upstream of the pump 123, and in this case downstream of the IVC flow sensor 125, and the other end connected to the pressure control duct 142 so that fluid can flow from the pressure control duct 142 to the IVC duct 104, bypassing the organ. A blood gas analyser (BGA) 192 is arranged to measure various parameters of the fluid flowing through the fluid analysis duct 190. In this embodiment the BGA 192 is arranged to measure the oxygen content and the carbon dioxide content of the fluid flowing through it. Other parameters can also be measured and monitored. The BGA 192 is connected to the controller 18 and arranged to output signals each of which is indicative of the value of one of the parameters it measures, and the controller 18 is arranged to receive those signals so that the parameters can be monitored by the controller 18. The signals therefore include an oxygen level signal, a $CO_2$ level signal, and a glucose level signal in this embodiment.

Figure 3:
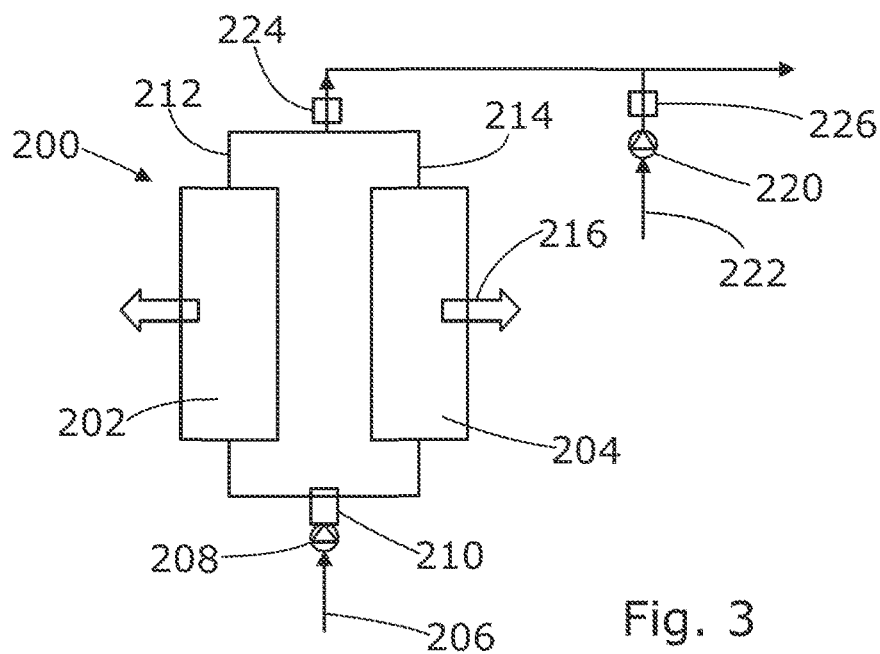
FIG. 3 is a schematic diagram of an oxygen concentrator forming part of the system of FIG. 1.

Referring to FIG. 3, the oxygen supply to the oxygenator inlet 154 is provided by an oxygen concentrator 200. This comprises a pair of zeolite towers 202, 204, an air inlet 206 arranged to receive gas in the form of air at atmospheric pressure, a compressor 208 arranged in the inlet to compress the incoming air, and a two way switch valve 210 operable to control the flow of incoming air into the zeolite towers 202, 204. Each of the towers 202, 204 has an outlet 212, 214 and these are connected together to form a single outlet from the oxygen concentrator which in turn is connected to the inlet 154 of the oxygenator. In use, as the compressed air flows through the zeolite towers 202, 204, the zeolite extracts nitrogen from the air which increases the concentration of oxygen in the gas. The nitrogen leaves the towers via vents 216, and the gas leaving the concentrator 200 through its outlet, which comprises concentrated oxygen as well as some nitrogen and traces of other gases, is fed to the oxygenator inlet 154. A proportional valve 224 in the outlet from the oxygen concentrator is arranged to control the flow rate of gas, and hence oxygen, from the oxygen concentrator 200 to the oxygenator 14. The proportional valve 224 is connected to, and controlled by, the controller 18 so that the controller can control the flow rate of oxygen into the oxygenator 14. The air supply to the oxygenator inlet 154 is provided by a further compressor 220 which has an inlet 222 arranged to receive air at atmospheric pressure. A further proportional valve 226 in the outlet from the compressor 220 is connected to and controlled by the controller 18, so that the controller can control the flow rate of air from the compressor 220 to the oxygenator. Because there are separate proportional valves for the oxygen and air supplies, the flow rates of oxygen and air can be controlled, at least to some extent, independently of each other.

In a modification to the arrangement of FIG. 3, the second compressor 220 is omitted and the output from the first compressor 208 is connected both to the oxygen concentrator 200 and through a separate air duct via the second proportional valve 226 to the oxygenator gas inlet. The single compressor 208 therefore provides the pressure for the oxygen and air supplies, the flow rates of which are controlled independently by their respective flow control valves 224, 226.

Referring back to FIG. 1, perfusate fluid flow through the liver is controlled by the controller 18 which is arranged to control the pressure in the hepatic artery duct 102 and the IVC duct 104 to maintain them at approximately constant pressures, allowing the liver to regulate the flow rate of fluid through it itself. To do this, the controller 18 is arranged to monitor the pressure in the hepatic artery duct 100 by monitoring the output signal from the pressure sensor 136 and the pressure in the vena cava duct 104 by monitoring the output of the pressure sensor 138, and to control the perfusion pump 123 and the pinch valve 146 in the pressure control duct 142 so as to maintain the measured pressures, i.e. the pressure sensor output signals, at respective set levels, or within respective ranges.

The oxygen level in the perfusate fluid is also controlled by the controller 18 during perfusion. While most of the oxygenated perfusate from the oxygenator outlet 114 flows through the hepatic artery duct 102, a small proportion of it is diverted through the fluid analysis duct 190 and through the BGA 192. The BGA 192 detects the level of oxygen in the perfusate, which is monitored by the controller 18. The controller 18 is arranged to control the pressure and flow rate of oxygen supplied by the oxygen concentrator 200 to the oxygenator by controlling the pump 208 and the two-way valve 210 of the oxygen concentrator 200, so as to control the rate at which perfusate is oxygenated in the oxygenator 100. The controller 18 is arranged to keep the oxygen level of the blood at a predetermined level or within a predetermined range. The controller 18 has a memory in which a target level or range of the oxygen content can be stored and the controller is arranged to compare the measured level with the stored level to determine how the oxygen level needs to be controlled. Typically the complete range will be defined, with upper and lower limits of oxygen content. However the range may be defined only by a lower limit, in which case the controller can be arranged to trigger a process to add oxygen to provide a step increase in oxygen content when the oxygen content falls below that level. The stored target level or range can be selected and altered by means of a user input which in this case is in the form of a graphic user interface (GUI) 17 connected to the controller 18. The GUI 17 is also arranged to display various information including the values of various operating parameters of the system, which in this embodiment include oxygen level, $CO_2$ level, glucose level, temperature, and flow rate of the perfusate.

The carbon dioxide ($CO_2$) level in the perfusate is also monitored and controlled by the controller 18 in a similar way to the oxygen level, except that it is arranged to increase the flow rate of air to reduce the $CO_2$ level, decrease the flow rate of air to increase the $CO_2$ level. The controller 18 is arranged to continuously use the $CO_2$ level signal from the BGA 192 to measure the $CO_2$ level in the perfusate, compare it with target levels stored in memory in the controller 18, and control the air flow control valve 226 to control the flow rate of air into the oxygenator 16. Varying the flow rate of air varies the rate at which $CO_2$ is extracted from the perfusate, so controlling the air flow rate through the oxygenator can be used to control the $CO_2$ level in the perfusate. If the $CO_2$ level is above the target range, then the flow rate of air is increased so as to increase the rate at which $CO_2$ is extracted from the perfusate. If the $CO_2$ level is below the target range, then the air flow rate is decreased to decrease the rate at which $CO_2$ is extracted from the perfusate. The target $CO_2$ level or range can also be set and adjusted by a user by means of the user input 17.

In the embodiment described above, the system is arranged for perfusion of a liver. However other organs such as the kidney can be perfused, and such organs only have one artery to supply blood to the organ and one vein to take blood from the organ. Therefore in another embodiment the system is the same as that described above except that the portal vein duct is completely omitted.

The invention claimed is:

1. A perfusion system for the perfusion of an organ, the system comprising:
    a perfusion fluid circuit for circulating perfusion fluid through the organ;
    an oxygenator for adding oxygen into the perfusion fluid, the oxygenator comprising a duct to carry the perfusion fluid, an oxygen chamber, and a permeable membrane between the duct and the oxygen chamber;
    an oxygen supply arranged to supply oxygen to the oxygenator, wherein the oxygen supply comprises an oxygen concentrator, the oxygen concentrator comprising an inlet arranged to receive gas in the form of air, a compressor arranged in the inlet, and a nitrogen extractor arranged to extract nitrogen from the gas thereby to increase the oxygen concentration of the gas;
    an air supply arranged to supply air to the oxygenator;
    a carbon dioxide sensor arranged to measure a carbon dioxide content of the perfusion fluid;
    an air control valve arranged to control the flow rate of air from an air supply to the oxygen chamber;
    an oxygen control valve arranged to control the flow rate of oxygen from the oxygen concentrator to the oxygen chamber;
    an oxygen sensor arranged to measure an oxygen content of the perfusion fluid; and
    a controller arranged to define a first target range for said oxygen content, monitor the measured oxygen content and to control the oxygen control valve and the compressor in response to the measured oxygen content thereby to maintain the oxygen content within the first target range, and to define a second target range for said carbon dioxide content, to monitor the measured carbon dioxide content and to control the air control valve in response to the measured carbon dioxide content thereby to maintain the carbon dioxide content within the second target range.

2. A perfusion system according to claim 1, wherein the compressor is arranged to pump the gas through the nitrogen extractor, and to pump gas to the oxygenator, bypassing the nitrogen extractor, thereby to form the air supply.

3. A perfusion system according to claim 1 further comprising a user interface arranged to enable a user to input at least one limit of said range, or at least one of said ranges.

4. A perfusion system according to claim 1 further comprising an analysis duct through which the perfusion fluid can flow to bypass the organ, wherein a measuring means is arranged to measure the perfusion fluid in the analysis duct.

5. A perfusion system according to claim 1 wherein the oxygen sensor and the carbon dioxide sensor are arranged to operate during perfusion of the organ and the controller is arranged to operate during perfusion of the organ to maintain the target ranges.

6. A perfusion system for the perfusion of an organ, the system comprising:
   a perfusion fluid circuit for circulating a warm perfusion fluid through the organ;
   an oxygenator for adding oxygen into the perfusion fluid, the oxygenator comprising a duct to carry the perfusion fluid, an oxygen chamber, and a permeable membrane between the duct and the oxygen chamber;
   an oxygen supply arranged to supply oxygen to the oxygenator, wherein the oxygen supply comprises an oxygen concentrator, the oxygen concentrator comprising an inlet arranged to receive gas in the form of air, a compressor arranged in the inlet, and a nitrogen extractor arranged to extract nitrogen from the gas thereby to increase the oxygen concentration of the gas;
   an air supply arranged to supply air to the oxygenator;
   a carbon dioxide sensor arranged to measure a carbon dioxide content of the perfusion fluid;
   an air control valve arranged to control the flow rate of air from an air supply to the oxygen chamber;
   an oxygen control valve arranged to control the flow rate of oxygen from the oxygen concentrator to the oxygen chamber;
   an oxygen sensor arranged to measure an oxygen content of the perfusion fluid;
   a heater to heat the perfusion fluid;
   a thermometer to measure the temperature of the perfusion fluid; and
   a controller arranged to define a first target range for said oxygen content, monitor the measured oxygen content and to control the oxygen control valve and the compressor in response to the measured oxygen content thereby to maintain the oxygen content within the first target range, and to define a second target range for said carbon dioxide content, to monitor the measured carbon dioxide content and to control the air control valve in response to the measured carbon dioxide content thereby to maintain the carbon dioxide content within the second target range.

* * * * *